United States Patent [19]

Lau

[11] Patent Number: 4,952,519

[45] Date of Patent: Aug. 28, 1990

[54] PROTEIN IMMOBILIZATION WITH POLY(ETHYLENEIMINE) DERIVATIZED WITH A HYDROPROBIC GROUP

[75] Inventor: Phillip H. Lau, Hockessin, Del.

[73] Assignee: E. I. Du Pont de Nemours and Company, Wilmington, Del.

[21] Appl. No.: 188,956

[22] Filed: May 2, 1988

[51] Int. Cl.$^5$ ............... G01N 33/547; G01N 33/538; G01N 33/53; C12N 11/06

[52] U.S. Cl. .......................... 436/532; 435/7; 435/180; 435/181; 435/815; 436/530; 436/541; 436/824

[58] Field of Search ............... 435/7, 174, 177, 180, 435/181; 436/531, 532, 533, 534, 541, 824

[56] References Cited

U.S. PATENT DOCUMENTS

| | | | |
|---|---|---|---|
| 3,619,371 | 11/1971 | Crook et al. | 195/63 R |
| 3,796,634 | 3/1974 | Haynes et al. | 435/180 |
| 3,846,306 | 11/1974 | Barker et al. | 210/196 C |
| 4,001,583 | 1/1977 | Barrett | 250/303 |
| 4,006,059 | 7/1977 | Butler | 435/176 |
| 4,045,384 | 8/1977 | Dorman | 260/8 |
| 4,085,005 | 4/1978 | Bleha et al. | 195/68 |
| 4,119,589 | 10/1978 | Horn et al. | 260/6 |
| 4,176,006 | 11/1979 | Cormier et al. | 435/74 |
| 4,220,565 | 9/1980 | Katz | 260/6 |
| 4,245,005 | 1/1981 | Regnier et al. | 428/420 |
| 4,253,995 | 3/1981 | Katz | 260/6 |
| 4,253,996 | 3/1981 | Katz | 260/6 |
| 4,278,651 | 7/1981 | Hales | 435/1 |
| 4,279,787 | 7/1981 | Huizinga | 260/8 |
| 4,286,964 | 9/1981 | Seed | 23/230 B |
| 4,352,884 | 10/1982 | Nakashima et al. | 435/180 |
| 4,418,152 | 11/1983 | Hosaka et al. | 436/511 |
| 4,419,444 | 12/1983 | Quash | 435/7 |
| 4,444,879 | 4/1984 | Foster et al. | 435/7 |
| 4,582,810 | 4/1986 | Rosenstein | 436/528 |
| 4,609,707 | 9/1986 | Nowinski et al. | 524/54.1 |
| 4,615,985 | 10/1986 | Deutsch et al. | 436/531 |
| 4,619,897 | 10/1986 | Hato et al. | 435/182 |
| 4,654,299 | 3/1987 | Lentfer | 435/7 |
| 4,657,873 | 4/1987 | Gadow et al. | 436/532 |
| 4,681,843 | 7/1987 | Egerer et al. | 435/41 |
| 4,753,983 | 6/1988 | Ngo | 435/181 X |
| 4,808,530 | 2/1989 | Meang et al. | 435/180 |

FOREIGN PATENT DOCUMENTS

| | | |
|---|---|---|
| 97898 | 1/1984 | European Pat. Off. . |
| 83109418.0 | 4/1984 | European Pat. Off. . |
| 221308 | 5/1987 | European Pat. Off. . |
| WO83/02954 | 9/1983 | PCT Int'l Appl. . |

OTHER PUBLICATIONS

Kitagawa, J., of Chromatography, vol. 443, Nov. 2–4, 1987, Part 1. Abstract.

Atkinson et al., Biochemica et Biophysica Acta, 308 (1972) 41–52.

Kitagawa, J. of Chromatography, vol. 443, pp. 133–141 (1988).

Gadow et al., J. Clin. Chem. Clin. Biochem., pp. 789–797, vol. 21, No. 12 (1983).

Weetal, Methods in Enzymology, vol. XLIV, Immobilized Enzymes, Chap. 10, 134, Ed. K. Mosbach, Acad. Press, NY (1976).

Messing, Methods in Enzymology, vol. XLIV, Immobilized Enzymes, Chap 11, 149, Ed. K. Mosbach, Acad. Press, NY (1976).

Zouali, et al., J. Immunological Methods, pp. 105–110, vol. 90 (1986).

Kaul et al., J. Chromatography, pp. 339–346, vol. 438, (1988).

*Primary Examiner*—David M. Naff

[57] ABSTRACT

A member of a bioaffinity binding pair is immobilized on a plastic surface by coating the surface with poly(ethyleneimine) derivatized with a hydrophobic group, and covalently coupling the member to the coated surface. The immobilized member may be used in immunoassays or bioaffinity separations. The derivatized poly(ethyleneimine) is preferably tosyl poly(ethyleneimine).

13 Claims, No Drawings

PROTEIN IMMOBILIZATION WITH POLY(ETHYLENEIMINE) DERIVATIZED WITH A HYDROPROBIC GROUP

FIELD OF THE INVENTION

This invention relates to preactivating plastic surfaces with poly(ethyleneimine) derivatized with a hydrophobic group and, more particularly, to the use of these preactivated surfaces in bioaffinity separations and immunoassays.

BACKGROUND

Affinity separations utilize the natural affinity that one molecule has for another molecule to effect a separation. Bioaffinity separations are defined as affinity separations in which one of the components is of biological interest or has biological activity. Thus, bioaffinity separations involve at least one biomacromolecule, such as a protein or nucleic acid, as one of the components of the binding pair. Examples of bioaffinity binding pairs include, but are not limited to, the following: antigen-antibody, substrate-enzyme, effector-enzyme, inhibitor-enzyme, complementary nucleic acid strands, binding protein-vitamin, binding protein-nucleic acid, reactive dye-protein, reactive dye-nucleic acid, biotin-avidin and Protein A—IgG.

Bioaffinity separations are conducted on bioaffinity selective adsorbent to which a member of the bioaffinity binding pair has been attached either covalently or by non-specific adsorption. The other member of the binding pair then binds to its counterpart when it is placed in contact with this bioaffinity selective adsorbent. Once the members of the bioaffinity binding pair have bound each other, then the member which is not placed in contact with the bioaffinity selective adsorbent can be eluted with a wide number of reagents, depending upon the experimental parameters.

Weetal, Methods in Enzymology, Volume XLIV; Immobilized Enzymes, Chapter 10, 134, Ed. K. Mosbach, Academic Press, NY (1976), describes various approaches by which to covalently modify inorganic carrier surfaces. Although covalent attachment of a member of a bioaffinity binding pair is preferred, it has some disadvantages, such as, increased nonspecific binding of undesirable proteins to the immobilized molecule, alteration of the binding properties of the covalently attached molecule and inability to recover scarce or expensive molecules because the molecule is irreversibly bound to the carrier.

Messing, Methods in Enzymology, Volume XLIV: Immobilized Enzymes, Chapter 11, 149, Ed. K. Mosbach, Academic Press, NY (1976), sets forth another commonly used attachment technique, nonspecific adsorption of a member of a bioaffinity binding pair to the carrier. This technique also has disadvantages such as the inability to retain the nonspecifically adsorbed molecule on the carrier due to the weak forces binding the molecule to the support. Another problem is partial alteration of the binding properties of the molecule adsorbed to the carrier.

Other approaches have been developed in the art for immobilizing biological molecules to a plastic surface by physically or chemically derivatizing the surfaces.

U.S. Pat. No. 4,657,873 issued to Gadow et al. on Apr. 14, 1987, discloses preactivation of plastic surfaces by coating the surface with an amphoteric polypeptide consisting of phenylalanine and lysine amino acids. The hydrophobic phenylalanine residues enable the polypeptide to adsorb to the plastic surface and the hydrophilic lysine residues are available for immobilizing organo-chemical and biological materials. One problem with the Gadow approach is that the polypeptide of interest is not readily available and is very expensive to obtain. In addition, polypeptides may be susceptible to attack by proteases which may be present in clinical samples. Whether proteases will degrade a polypeptide coated on a plastic surface depends on the tertiary structure of the polypeptide on the surface. If inadvertent digestion of the polypeptide occurred, then a large error would be introduced into assay results.

Similarly, Gadow et al., J. Clin. Chem. Clin. Biochem., pages 789–797, vol. 21, no. 12 (1983), discloses the adsorption of poly phe-lys to polystyrene balls followed by activation with glutaraldehyde and coupling of the required ligand. This technique has the same deficiencies as the technique discussed above in connection with U.S. Pat. No. 4,657,873.

U.S. Pat. No. 4,654,299 issued to Lentfer on Mar. 31, 1987, discloses immobilizing proteins on polystyrene surfaces which have been preactivated with a bis-diazonium compound. The major drawback of this procedure is that bis-diazonium compounds and their precursors, benzidines, are highly carcinogenic.

U.S. Pat. No. 4,444,879, issued to Foster et al. on Apr. 24, 1984, discloses a solid-phase support for immobilizing reactants of an immunoreaction which comprises a light-transparent, water-insoluble article which is inert to chemical reaction with the reactants and a dried film of a synthetic, polymeric resin having chemical groups attached which are capable of forming covalent bonds with the reactants. At least a portion of the article is coated with the dried film.

U.S. Pat. No. 4,001,583, issued to Barrett on Jan. 4, 1977, discloses pretreating plastic surfaces with glutaraldehyde to covalently bind biological substances to the plastic surface. Glutaraldehyde is polymerized directly on the inside surface of a plastic material with or without previously treating the surface with an aliphatic amine or diamine.

U.S. Pat. No. 4,279,787, issued to Huizinga on July 21, 1981, discloses a method of binding antigenically active materials to the surface of water insoluble hydrophobic polymeric substances which comprises pretreatment with an aldehyde of the formula, OHC-X-CHO wherein X may be an alkylene or cycloalkyl group.

U.S. Pat. No. 4,352,884, issued to Nakashima et al. on Oct. 5, 1982, discloses a carrier coated with a hydrophilic acrylate copolymer for immobilizing bioactive materials.

U.S. Pat. No. 4,278,651, issued to Hales on July 14, 1981, discloses a solid support having a water insoluble polymer including at least one functional group through which a receptor is covalently linked to the support.

European patent application No. 83109418.0 discloses plasma modification techniques to chemically modify polymeric surfaces in order to attach large molecules.

SUMMARY OF THE INVENTION

This invention provides an alternative process for immobilizing biological materials on plastic surfaces utilizing poly(ethyleneimine) derivatized with a hydrophobic group which is relatively inexpensive to prepare, readily available, does not present an environmental threat and is not carcinogenic. The binding capacity of the plastic surface is substantially increased, the biological activity of the bound material is not significantly altered and the bound material is resistant to desorption.

Specifically, this invention pertains to poly(ethyleneimine) derivatized with a hydrophobic group preactivated plastic surfaces. It also relates to a method of preparing these surfaces, as well as to the use of these preactivated surfaces in immunoassays and bioaffinity separations.

DESCRIPTION OF THE INVENTION

A plastic carrier surface is coated with a solution of a poly(ethyleneimine) (PEI) derivatized with a hydrophobic group. Many different kinds of plastics including polystyrene, polyethylene, polypropylene and acrylic can be used in any number of forms, such as, microtiter plates, paddles, membranes, tubes, balls and lattices. The preferred plastic is polystyrene which can be used in the form of $\frac{1}{4}''$ balls, microtiter plates and coated tubes. These solid supports are most commonly used in heterogeneous immunoassays and bioaffinity separations.

Any number of hydrophobic groups known to those skilled in the art can be used to derivatize PEI. For example, there can be mentioned benzoyl groups and tosyl groups. The preferred compound of this invention is tosyl-PEI.

PEI is randomly formed and, thus, its structure does not consist of a uniform alignment of a particular monomeric unit. Even though this randomly oriented polymer is difficult to reduce to a single chemical formula, it can be prepared easily. For example, tosyl PEI was prepared by reacting poly(ethyleneimine) in water with tosyl chloride and purifying by dialysis or on a Sephadex ® gel filtration column. The resulting product is water soluble, very stable and not susceptible to protease degradation. The cost to prepare this compound is extremely low. It should also be understood that any number of poly(alkylamines), such as poly(propylamine), poly(butylamine) and the like derivatized with a variety of hydrophobic groups would be suitable for preactivating plastic surfaces.

Coating of the plastic surface with PEI derivatized with a hydrophobic group can be performed in a diluted aqueous solution. Coating can take place over the course of a few hours or coating can occur overnight. There are no temperature constraints, coating can occur at room temperature or at 4° C. The preferred conditions for coating a plastic surface are the following: overnight at room temperature using 100 micrograms/mL of coating reagent (as discussed in Example 3 below) in 0.1M phosphate buffer at pH 7.0.

Once the plastic surface is preactivated with poly(ethyleneimine) derivatized with a hydrophobic group, a member of a bioaffinity binding pair can be attached for subsequent use in heterogeneous immunoassays and bioaffinity separations. The following illustrates some bioaffinity binding pairs suitable for attachment to a plastic surface preactivated according to the invention; however, it should be noted that the following list is not exhaustive: antigen-antibody, enzyme substrate-enzyme, enzyme inhibitor-enzyme, enzyme effectors-enzyme, complementary nucleic acid strands, binding protein-vitamin, binding protein-nucleic acid, reactive dye-protein and reactive dye-nucleic acid, biotin-avidin and protein A-IgG. Furthermore, synthetic mimics of binding proteins such as polylysine and polyethyleneimines or other bimacromolecules capable of specific binding such as Protein A, Protein G and the like also fall within the scope of this invention. Either member of the binding pair can be immobilized depending upon the experimental design.

Coupling of a member of bioaffinity binding pair to the plastic surface coated with poly(ethyleneimine) derivatized with a hydrophobic group can be achieved using any number of homobifunctional and heterobifunctional cross-linking reagents well known to those skilled in the art. For example, glutaraldehyde, epichlorohydrin and toluene 2,4-diisocyanate are some of the available reagents. The preferred method of attaching a member of a bioaffinity binding pair to the preactivated surface of this invention is to react the member selected to be immobilized with the preactivated plastic surface and 5% glutaraldehyde for two hours at room temperature.

Members of bioaffinity binding pairs can be attached directly to poly(ethyleneimine) derivatized with a hydrophobic group or can be attached to carrier molecules which are then attached to the poly(ethyleneimine) derivatized with a hydrophobic group. In either case, once the member is immobilized on the preactivated plastic surface of this invention, it can then be used in a number of heterogeneous immunoassay formats as well as in bioaffinity separations as illustrated in Examples 7 and 8 below.

Of course, it is understood that many variations are possible and all fall within the scope of this invention.

The following examples are intended to illustrate the invention and are not to be construed as limitations thereon.

EXAMPLE 1

Preparation and Purification of Tosyl-Poly(ethyleneimine) (Tosyl-PEI)

Two grams of poly(ethyleneimine) (50% aqueous solution, Aldrich Chemical, Milwaukee, Wis.) was dissolved in 50 mL of distilled water. Tosyl chloride (0.1 g from Aldrich Chemical, Milwaukee, Wis.) and 2 mL of 18% potassium hydroxide were added to the PEI solution slowly and simultaneously with vigorous mixing. The mixture was stirred at room temperature for 2 hours, then dialyzed against distilled water and diluted to 100 mL.

EXAMPLE 2

Preparation and Purification of Benzoyl-Poly(allylamine hydrochloride) (Benzoyl-PAAH)

One gram of poly(allylamine hydrochloride) (high molecular weight, Aldrich Chemical, Milwaukee, Wis.) was dissolved in 20 mL of distilled water and the pH was adjusted to 8.0 using 6 N sodium hydroxide. 0.5 mL of benzoyl chloride (Aldrich Chemical, Milwaukee, Wis.) was added to the solution and the resulting mixture was stirred at room temperature for 2 hours. The white benzoic acid precipitate was removed by centrifugation, and the product was dialyzed against distilled water. The purity of the product was analyzed by passing 1 mL of the product through a Sephadex ® G-15 column (1×20 cm) and eluted with phosphate buffered saline (PBS pH 7.6). Based on the benzoyl group adsorption and free amino group assay on the pooled fractions, the purity of the benzoyl poly(allylamine) was estimated to be 94%.

EXAMPLE 3

Immobilization of Protein on Tosyl-PEI Coated Polystyrene Balls

A. Adsorption of tosyl-PEI on polystyrene balls

Fifteen ¼" polystyrene balls (Pierce Chemical Company, Rockford, Wis. 61105) were washed once with 50 mL of 0.1M phosphate buffer (pH 7.0). The balls were then mixed with 10 mL of 100 micrograms/mL tosyl-PEI (prepared in Example 1) in 0.1M phosphate buffer (pH 7.0) at room temperature overnight. The slightly cloudy solution became clear, indicating that the tosyl-PEI had been adsorbed on the polystyrene balls. The balls were washed five times with 5 mL of phosphate buffered saline (PBS, 10 mM phosphate buffer, 150 mM sodium chloride, pH 7.0) and were either used immediately or stored at 4° C.

B. Activation of tosyl-PEI coated polystyrene balls with glutaraldehyde

The 15 polystyrene balls prepared above were mixed with 5 mL of 5% glutaraldehyde (diluted from 25% solution from Sigma Chemical Company, St. Louis, Mo. 63178) at room temperature for 2 hours. After activation, the balls were washed three times with 10 mL of distilled water.

C. Immobilization of protein on activated polystyrene balls

Ten activated polystyrene balls (Example 3B) were mixed at room temperature overnight with 5 mL of 10 mM phosphate buffer (pH 7.0) containing 10 micrograms/mL to 100 micrograms/mL of protein depending on the kind of protein to be immobilized. After the reaction, the balls were washed three times with 10 mL of wash buffer (10 mM tris(hydroxymethyl)aminoethane, 0.1% Tween ® 20, 150 mM sodium chloride and 0.3% chloroacetimide, pH 9.0) and two times with 10 mL of PBS. The unreacted active sites of balls used in immunoassays were blocked with 2.5 mL of 1 mg/mL of bovine serum albumin (Sigma Chemical Company, St. Louis, Mo. 63178) in PBS for two hours at room temperature. After blocking, the balls were washed three times with 3×10 mL of wash buffer and twice with 10mL of PBS and stored in PBS at 4° C.

EXAMPLE 4

Comparison of Tosyl-PEI Immobilization Technique With Other Commonly Used Immobilization Techniques By Evaluating Total Protein Immobilized

A. Iodination of anti-alkaline phosphatase (anti-AP) monoclonal antibodies

3 mg of mouse anti-alkaline phosphatase monoclonal antibodies obtained from Jackson ImmunoResearch Laboratories (Avondale, Pa. 19311) was labeled with $125_I$-Bolton-Hunter Reagent (3.33 mCi/mL, 2220 Ci/mmole, (Du Pont, Wilmington, Del. 19898) according to the procedure of S. H. Snyder et al. (Journal of Biol. Chem., 251, 5680–5685, 1976). The specific activity of the labeled protein was approximately 0.018 microCurie/microgram.

B. Immobilization of $125_I$-anti-AP on Polystyrene Balls

2 mL of 100 micrograms/mL $125_I$-anti-AP prepared in Example 4A as described above, was used to coat five ¼" polystyrene balls according to the procedures below:

(1) Underivatized polystyrene balls, alkylamine balls, hydrazide balls, and Sanger reagent balls were all obtained from Pierce Chemical Company (Rockford, Wis. 61105). Succinyl alkylamine balls were prepared from alkylamine balls (Pierce Chemical Company, Rockford, Wis. 61105) and excess succinic anhydride according to the procedure recommended by Pierce Chemical Company (p. 48, Pierce 1986–87 Handbook and General Catalog). This procedure also set forth the protocol by which to attach protein to these succinylated alkylamine balls.

(2) $125_I$-anti-AP was coupled to tosyl-PEI coated polystyrene balls and benzoyl-PAAH coated polystyrene balls following the procedure in Example 3C.

(3) $125_I$-anti-AP was adsorbed to underivatized polystyrene balls by incubating the balls in the protein solution at room temperature overnight and washed and blocked according to the procedure in Example 3C.

(4) Protein was immobilized on poly(phenylalaninelysine) coated polystyrene balls according to the procedure described in U.S. Pat. No. 4,657,873, issued to Gadow et al.

(5) Protein was immobilized on toluene 2,4-diisocyanate coated polystyrene balls according to the procedure of T. Saito (Clinica Chimica Acta, 133, 301–310, 1983).

(6) Carboxylmethyl latex coated polystyrene balls were prepared by incubating 10 polystyrene balls with 5 mL of carboxylmethyl latex (Seragen Diagnostics, Inc., Indianapolis, Ind. 46206) for two hours at room temperature. After washing with PBS, they were activated with water soluble carbodiimide to which the $125_I$-labeled protein was coupled.

After protein coupling was completed, all the balls were washed four times with 5 mL of 80 mM sodium chloride and 0.1% Tween ® 20 (pH 6.0) and four times with 5 mL of 0.1 M sodium chloride. These balls were stored in 5 mL of 0.1 M sodium chloride.

C. Calculation of total amount of protein immobilized

Total amount of protein bound on the polystyrene balls were determined by counting the balls in a Beckman ® Gamma 800 Counting Systems (Beckman Instruments, Inc., Fullerton, Calif. 92634). The average counts from five balls were used to calculate the amount of protein based on a specific activity of 0.018 microCurie/microgram. The results are summarized in Table 1.

EXAMPLE 5

Activity of Enzyme Immobilized on Polystyrene Balls by Different Binding Techniques Beta-galactosidase (EIA grade from Boehringer Mannheim GmbH Biochemica, Federal Republic of Germany) was coupled to various activated polystyrene balls according to the various procedures set forth in Examples 4B(1)–4B(6). After washing to remove unbound enzyme, the enzyme activity on the balls was determined by adding 1 mL of enzyme substrate (2 mM o-nitrophenyl-galactopyranoside in 50 mM N-2-hydroxyethylpiperazine-N'-2-ethanesulphonic acid, HEPES, pH 7.7) to each ball and incubating at 37° C. for 10 minutes. The reaction was stopped by adding 1 mL of 0.1 M sodium carbonate buffer (pH 11.5) and the adsorbance at 406 nm was measured on a Hewlett Packard 8450 Diode Array Spectrophotometer (Hewlett Packard, Palo Alto, Calif. 94304). The adsorbance was directly proportional to the activity of the bound enzyme. The results are shown in Table 1.

EXAMPLE 6

Total Antibody Activity Bound on Polystyrene Balls by Different Binding Techniques The 125I-Anti-AP polystyrene balls prepared in Example 4 were used in this study. 2 mL of a 2 microgram/mL alkaline phosphatase (AP) (EIA grade from Boehringer Mannheim GmbH Biochemica, Federal Republic of Germany) was added to each ball and mixed at room temperature for 1.5 hours. The balls were washed four times with 5 mL of 80 mM sodium chloride and 0.1% Tween® 20 (pH 6.0) and four times with 5 mL of 0.1 M sodium chloride. The AP captured by the antibody immobilized on the balls was measured by adding 1 mL of enzyme substrate (15 mM 4-nitrophenyl phosphate (PNPP), 1 M diethanolamine and 0.5 mM magnesium chloride, pH 8.9) and incubating at 37° C. for 1 minute. The reaction was stopped by adding 1 mL of 0.5 M ethylenediaminetetraacetic acid (EDTA pH 9.0) and the adsorbance was measured on the HP 8450 Spectrophotometer as described in Example 5. The adsorbance is directly proportional to enzyme activity which is proportional to the activity of the immobilized antibody. The results are summarized in Table 1.

EXAMPLE 7

Human Chorionic Gonadotropin (Beta-HCG) Sandwich Enzyme Immunoassay Using anti-HCG Immobilized on Polystyrene Balls By Various Binding Techniques Mouse anti-HCG monoclonal antibodies (Hybritech, Inc., San Diego, Calif.) were immobilized on various activated polystyrene balls according to the procedures set forth in Example 4 above. 50 microliters of anti-HCG alkaline phosphatase monoclonal antibody conjugate and 100 microliters of HCG calibrators (both from E. I. du Pont de Nemours & Co., Wilmington, Del. 19898) were added to the anti-HCG coated balls and placed in a test tube. The mixture was mixed on a vibrator for 30 minutes at room temperature and the ball was washed three times with 2 mL of 80 mM sodium chloride and 0.1% Tween® 20 (pH 6.0). Two hundred microliters of the para-nitrophenylphosphate substrate as in Example 6 was added and incubated at 37° C. for 45 minutes. The reaction was stopped by adding 1 mL of stopping reagent (50 mM EDTA, pH 8.9) and the adsorbance at 406 nm was read on the HP 8450 spectrophotometer. The adsorbance at 0 mIU/mL (Background) and the adsorbance difference between and 200 mIU/mL concentration are shown in Table 1. Better assay performance is judged by the low background and high separation.

EXAMPLE 8

Immunoenzymometric Assay of Cyclosporin: Comparison of Adsorption Vs. Attachment Via Tosyl-PEI Coated Tube A. Preparation of Cyclosporin Conjugate Cyclosporin C succinimidyl succinate (Sandoz Ltd., Basle, Switzerland) was conjugated to human serum albumin (HSA) at a ratio of 1:10 (w/w) and dialyzed against PBS.

B. Adsorption of Conjugate to Underivatized Polystyrene Tube

The conjugate prepared above in step A was adsorbed on the walls of underivatized polystyrene tubes by incubating the protein solution at room temperature in the tubes overnight. Excess solution was washed away with wash buffer as described in Example 3C above and blocked according to the procedure outlined in Example 3C above.

C. Coupling of Conjugate to Tosyl-PEI Coated Polystyrene Tube

The conjugate prepared above in step A was coupled to a tosyl-PEI coated tube following the procedure outlined in Example 3C. The tosyl-PEI coated tubes were prepared and activated according to the procedures set forth in Examples 3A and 3B, respectively.

D. Preparation of Anti-Cyclosporin-Alkaline Phosphatase Conjugate 6.44 mg of monoclonal cyclosporin antibody (Sandoz, Ltd., Basle, Switzerland) was coupled to 9.82 mg of alkaline phosphatase using 15 mole excess of succinimidyl-4-(N-maleimidomethyl)-cyclohexane-1-carboxylate (Pierce Chemical Company, Rockford, Ill. 61105) at room temperature for 2 hours and purified on a gel filtration high performance liquid chromatograph.

E. Assay Protocol 400 microliters of distilled water, 100 microliters of whole blood sample or calibrator containing cyclosporin and 500 microliters of an anti-cyclosporin-alkaline phosphatase conjugate as described in step B were added to coated tubes as prepared in steps B and C. The cyclosporin calibrators contained cyclosporin concentrations of 0, 0.5, and 1.0 micrograms/ml. The mixtures were mixed for ten minutes at 37° C. The tubes were washed four times with 5 mL of distilled water.

F. Quantitation of Enzyme Bound to Tubes

The enzyme bound to the tubes was determined using two different approaches:

(1) In Tube Determination. The first determination involved a straight immunoenzymometric quantitation. 4 mL of PNPP substrate was added to the tubes and mixed at 25° C. for 4 minutes. The reaction was stopped by decanting the mixture into 4 mL of 3N sodium hydroxide. The adsorbance was measured at a wavelength of 406 nm using an HP 8450 spectrophotometer.

(2) Release Method. The second determination involved adding a release reagent which is a reagent capable of separating the cyclosporin conjugate prepared in step A from the surface of the tube to which it is attached. The purpose of adding the release reagent is to determine how tightly the cyclosporin conjugate bound to the tube surface. 1.1 mL of release reagent (0.05% Tween® 20 in 1M diethanolamine, pH 9.0) was added to the tubes and mixed at 37° C. for 10 minutes. 1 mL of the reagent was then removed from the tube and added to 3 mL of PNPP substrate. This mixture was incubated at 25° C. for 4 minutes. The reaction was stopped with 4 mL of 3N sodium hydroxide. The adsorbance was measured at a wavelength of 406 nm using an HP 8450 spectrophotometer.

(3) Results.

Table 2a sets forth the adsorbances recorded for enzyme bound to the tubes as determined by the two quantitation methods discussed in step F.

Table 2b sets forth a comparison of ratios (calculated as discussed below) for each concentration of cyclosporin which shows that the tosyl-PEI preactivated surface tightly binds the protein and is not susceptible to attack by the releasing reagent, whereas the protein which is merely adsorbed to non-preactivated tube surface is readily removed by the release reagent.

The ratios presented in Table 2b were calculated as follows:

A ratio of adsorbances was obtained for the adsorption coating tube as determined by the release and in tube method. Thus, for a 0 ug/mL concentration of cyclosporin, the 0.68 adsorbance obtained by the release method is divided by the 0.68 adsorbance obtained by the in tube method. The ratio is 1.0.

For the 0.1 microgram/mL concentration of cyclosporin, the 0.43 adsorbance obtained by the release method is divided by the 0.36 adsorbance obtained by the in tube method. This ratio is 1.19.

For the 0.5 microgram/mL concentration of cyclosporin, the 0.30 adsorbance obtained by the release method is divided by the 0.29 adsorbance obtained by the in tube method. This ratio is 1.03.

Similarly, ratios were obtained for assays conducted using tosyl-PEI coated tubes. The ratios at 0, 0.1 and 0.5 microgram/mL were 0.12, 0.13, and 0.14, respectively.

It is these ratios which are compared in Table 2b. The higher ratios reflect how easily the cyclosporin conjugate was released from the non-preactivated tube surface.

TABLE 1

Comparison of Protein Immobilization Methods

| Ball Type (Activation Method) | Ex. 4 Total Protein (μg Anti-AP) | Ex. 5 Enzyme Activity (ΔA$_{406}$/min.) | Ex. 6 Antibody Activity (A$_{406}$) | Ex. 7 HCG Assay Performance (Separation/Background) |
|---|---|---|---|---|
| Plain (Adsorption) | 1.0 | 0.207 | 0.147 | 327/40 |
| Tosyl-PEI* | 5.2 | 0.995 | 0.255 | 1057/55 |
| Benzoyl-PAAH* | ** | 0.40 | ** | 602/50 |
| Alkylamine* | 2.6 | 0.640 | 0.054 | 327/62 |
| Alkylamine (carbodiimide) | 5.9 | 0.237 | 0.240 | 52/52 |
| Sanger | 6.5 | 0.203 | 0.051 | 100/200 |
| Hydrazine* | 5.3 | 0.014 | 0.007 | 197/59 |
| Poly(phe-lys)* | ** | 0.969 | ** | 1190/55 |
| Toluene 2,4-diisocyanate | 1.2 | 0.092 | 0.030 | 265/138 |
| Carboxylmethyl latex (carbodiimide) | 1.8 | 0.152 | 0.067 | 15/41 |

*(glutaraldehyde)
**Benzoyl-PAAH and poly(phe-lys) were not available at the time the experiment was performed.

TABLE 2a

Immunoenzymometric Assay of Cyclosporin
Comparison of Tube Coating Methods

| Coating Method | Assay Method | Cyclosporin Level (Absorbance at 406 nm) | | |
|---|---|---|---|---|
| | | 0 | 0.1 | 0.5 μg/mL |
| Adsorption | In Tube* | 0.68 | 0.36 | 0.29 |
| Adsorption | Release** | 0.68 | 0.43 | 0.30 |
| Tosyl-PEI (glutaraldehyde) | In Tube* | 2.51 | 1.53 | 0.96 |
| Tosyl-PEI (glutaraldehyde) | Release** | 0.31 | 0.20 | 0.13 |

*Method 1
**Method 2

TABLE 2b

Comparison of Protein Immobilization Methods:
Preactivation with Tosyl-PEI Vs. No Preactivation
The figures reported below reflect how easily protein can be released from a nonpreactivated surface. The higher the ratio the more easily the protein is removed. The ratios were calculated according to the method discussed in Example 8F(3).

| Cyclosporin Level | Preactivation with Tosyl-PEI | | No Preactivation |
|---|---|---|---|
| 0.0 microgram/mL | 0.12 | vs. | 1.00 |
| 0.1 microgram/mL | 0.13 | vs. | 1.19 |
| 0.5 microgram/mL | 0.14 | vs. | 1.03 |

I claim:

1. A method for preactivating a plastic surface and for immobilization of a member of a bioaffinity binding pair comprising:
   (a) coating the surface with a solution or suspension of poly(ethyleneimine) derivatized with a hydrophobic group; and
   (b) covalently coupling the member of the bioaffinity binding pair to the product of step (a).

2. A method according to claim 1 wherein the hydrophobic group is a tosyl group.

3. A method according to claim 1 wherein the bioaffinity binding pair is selected from the group consisting of antigen-antibody, substrate-enzyme, effector-enzyme, inhibitor-enzyme, complementary nucleic acid strands, binding protein-vitamin, binding protein-nucleic acid, reactive dye-protein and reactive-dye-nucleic acid, biotin-avidin and protein A-IgG.

4. A method according to claim 1 wherein the plastic surface is polystyrene.

5. A preactivated plastic surface containing an immobilized member of a bioaffinity binding pair prepared by the method of claim 1.

6. A plastic surface according to claim 5 wherein the hydrophobic group is a tosyl group.

7. A plastic surface according to claim 5 wherein said plastic is polystyrene.

8. An assay for detecting or quantitating a substance in a sample suspected or known to contain said substance, said assay comprising:
   (a) contacting the sample with a member of a bioaffinity binding pair specific for the substance to be detected or quantitated which is immobilized on the surface of a plastic support by preactivating the surface with a coating of poly(ethyleneimine) derivatized with a hydrophobic group and covalently coupling to the coating the member of the bioaffinity binding pair; and
   (b) detecting or quantitating the substance.

9. An assay according to claim 8 wherein the hydrophobic group is a tosyl group and covalent coupling is by reacting with glutaraldehyde.

10. An assay according to claim 8 wherein the bioaffinity binding pair is selected from the group consisting of antigen-antibody, substrate-enzyme, effector-enzyme, inhibitor-enzyme, complementary nucleic acid strands, binding protein-vitamin, binding protein-nucleic acid, reactive dye-protein and reactive-dye-nucleic acid, biotin-avidin and protein A-IgG.

11. An assay according to claim 8 wherein the product of step (a) is reacted with a second member of the bioaffinity binding pair, said second member being labelled, to form a labelled complex which is then detected or quantitated.

12. An assay according to claim 8 wherein the sample is reacted with a labelled member of the bioaffinity binding pair to form a labelled complex which is then reacted with the immobilized member of the binding pair prior to detection or quantitation.

13. A method for performing a bioaffinity separation comprising:
  (a) capturing a substance on a bioaffinity selective adsorbent having a member of a bioaffinity binding pair covalently immobilized on a plastic support coated with poly (ethyleneimine) derivatized with a hydrophobic group wherein the immobilized member of the bioaffinity binding pair is specific for the substance; and
  (b) separating the captured substance from the member of the bioaffinity binding member.

* * * * *